United States Patent [19]

Pearson

[11] 4,133,838

[45] Jan. 9, 1979

[54] PROCESS FOR PREPARING HYDROCARBONS FROM METHANOL AND PHOSPHORUS PENTOXIDE

[75] Inventor: Donald E. Pearson, Nashville, Tenn.

[73] Assignee: Pearson Research Corp., Nashville, Tenn.

[21] Appl. No.: 577,643

[22] Filed: May 15, 1975

[51] Int. Cl.² ............................................. C07C 1/24
[52] U.S. Cl. ........................... 260/666 P; 260/676 R; 260/668 R; 260/682
[58] Field of Search ...... 260/676 R, 682 R, 683.15 C, 260/668 R, 666 P

[56] References Cited

U.S. PATENT DOCUMENTS

| | | | |
|---|---|---|---|
| 2,299,844 | 10/1942 | Ocon ................................ | 260/676 R |
| 2,373,475 | 4/1945 | Jean ................................... | 260/682 |
| 2,492,984 | 1/1950 | Grosse et al. ................... | 260/676 R |
| 3,275,698 | 9/1966 | Parish ............................... | 260/682 |
| 3,911,041 | 10/1975 | Kaeding et al. ................. | 260/682 |

*Primary Examiner*—Herbert Levine
*Attorney, Agent, or Firm*—Kane, Dalsimer, Kane, Sullivan and Kurucz

[57] ABSTRACT

A novel process is disclosed for preparing hydrocarbon mixtures from methanol or trimethyl phosphate. The process comprises heating the methanol or trimethyl phosphate with phosphorus pentoxide, polyphosphoric acid or a species of polyphosphoric acid intermediate between the two reagents at a temperature of circa. 185° C. to 300° C. The hydrocarbon mixtures obtained are useful fuel and lubricant compositions.

12 Claims, 1 Drawing Figure

PROCESS FOR PREPARING HYDROCARBONS FROM METHANOL AND PHOSPHORUS PENTOXIDE

BACKGROUND OF THE INVENTION

1. Field of the Invention

The invention concerns a process for synthesizing hydrocarbons by dehydration of acyclic alkanols and more particularly concerns the synthesis of hydrocarbon fuel and lubricant compositions from methanol or trimethyl phosphate.

2. Brief Description of the Invention

World attention has now focused upon the need for development of economical processes for the synthesis of hydrocarbon fuels and lubricants from readily available raw materials. Many of the previously suggested synthetic schemes are currently under renewed investigation to develop or improve a means whereby independence from the traditional petroleum sources of hydrocarbon fuels and lubricants can be achieved.

The dehydration of alkanols having at least 2 carbon atoms, to obtain mixtures of hydrocarbons was reported prior hereto; see for example U.S. Pat. Nos. 2,373,475 and 3,501,546. The former patent disclosure is particularly significant since the patentee dehydrated a wide range of acyclic alkanols with phosphoric acid to obtain hydrocarbon mixtures, but expressly excluded methanol as a starting material in his process of dehydration. In U.S. Pat. No. 1,895,529 the patentee taught dehydration of acyclic alkanols with oxide dehydrating agents such as the oxides of aluminum and thorium to obtain hydrocarbons. However, in regard to the dehydration of methanol, the patentee stated that the product obtained by his process was dimethyl ether and not a hydrocarbon which would be useful as a combustible fuel or lubricant.

Subsequently, Grosse et al. disclosed in U.S. Pat. No. 2,492,984 that methanol could be converted to branched chain hydrocarbons under specific temperature conditions in the presence of a dehydrating agent such as zinc chloride. Although nebulous, there is a teaching which could be construed as equating phosphoric acid to the zinc chloride in this reaction, but the patentee provided no working examples or details of procedure for one skilled in the art to follow and it would appear that any product mixture obtained would not be expected to include aromatics or cycloaliphatic compounds, a desirable fuel composition component.

More recently, U.S. Pat. Nos. 2,793,241 and 2,744,151 have described the conversion of methanol to hydrocarbon waxes by heating under super-atmospheric pressures in the presence of cobalt or molybdite catalysts.

Methanol is a relatively inexpensive compound, available in relative abundance. By the process of my invention it may be readily converted to hydrocarbon compositions which are useful fuels and lubricants. The process of the invention is particularly advantageous in that it produces high product yields, may be carried out under atmospheric pressure, requires relatively little energy input, uses reagents which are relatively abundant, yields a pure product which is readily separated from the reaction mixture without the use of expensive and complicated separatory techniques and is relatively non-hazardous to practice.

Subsequent to my invention, the process of the invention was disclosed by me in J.C.S. Chem. Comm., 1974, page 397.

SUMMARY OF THE INVENTION

The invention comprises a process for preparing a mixture of hydrocarbons, which comprises; heating a mixture comprising in a molar ratio of from about 1:1 to 1:2.2, phosphorus pentoxide and a compound selected from methanol, trimethyl phosphate and mixtures thereof, to a temperature within the range of from about 185° C. to about 300° C.

Figure 1:
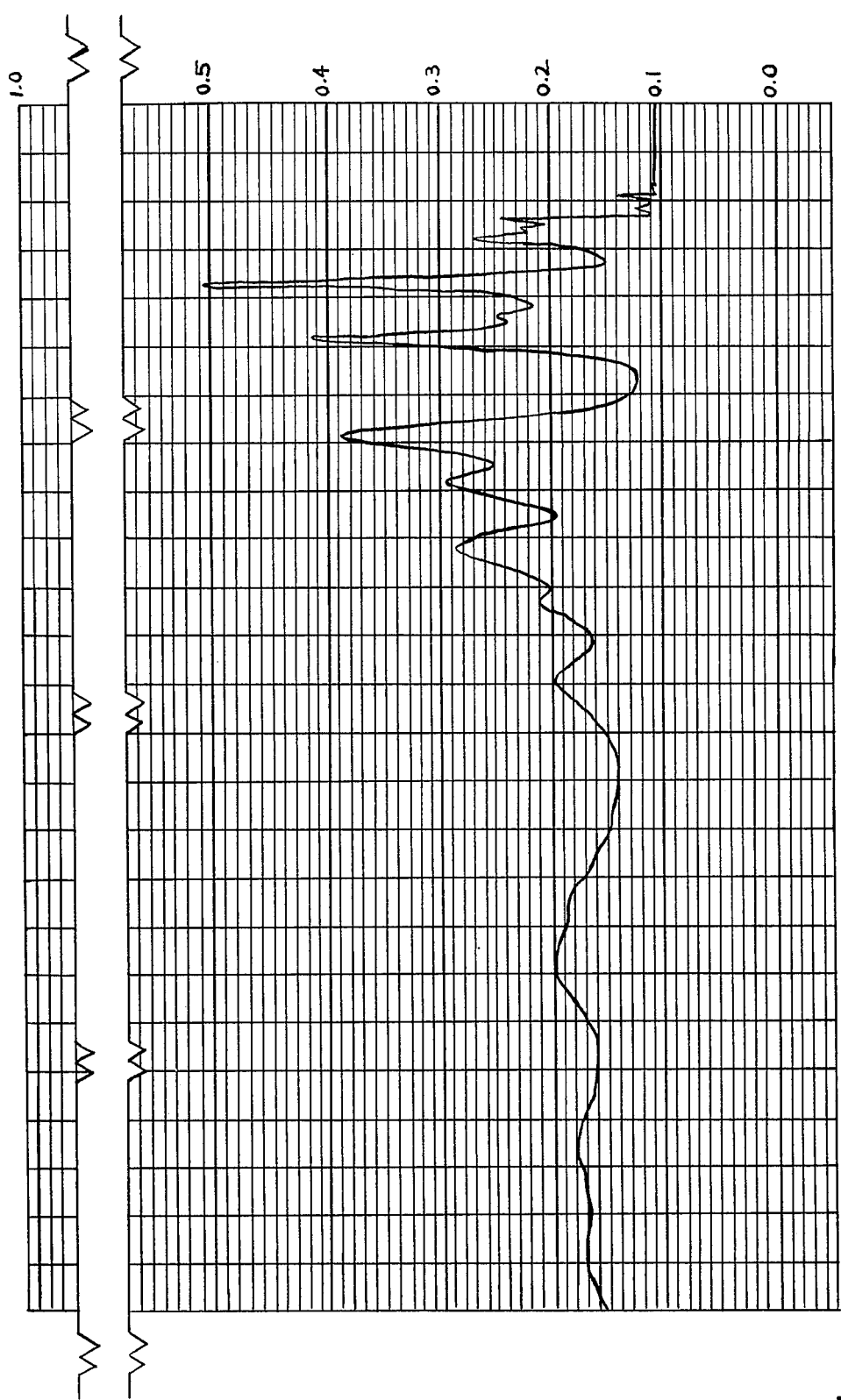
FIG. 1 shows a gas-liquid chromatogram showing the spectra of an aliquot of the product of the invention as obtained in Example 2.

The process of the invention is useful to prepare a novel mixture of hydrocarbons, including alkanes, cycloalkanes, alkenes, aromatic and alkyl-substituted aromatic compounds. Although the component compounds found in the hydrocarbon mixtures produced by the process of the invention are known compounds, the mixtures themselves appear to be unique to the process of the invention. The novel compositions are useful fuel compositions and lubricants.

DETAILED DESCRIPTION OF THE INVENTION

The starting materials employed in the process of the invention are essentially phosphorus pentoxide, methanol and/or trimethyl phosphate. The preferred source of phosphorus pentoxide for use in the process of the invention is polyphosphoric acid and in a preferred embodiment of the invention the methanol or trimethyl phosphate is admixed with polyphosphoric acid containing from about 78% to about 84% by weight of phosphorus pentoxide, under the conditions of the process of the invention. In a preferred embodiment of the invention, additional phosphorus pentoxide may be added to the polyphosphoric acid.

The chemical reaction which occurs upon admixture of methanol with the phosphorus pentoxide or polyphosphoric acid is not completely understood. It is believed however that an intermediate in the ultimate conversion to hydrocarbons may be monomethyl, dimethyl or trimethyl phosphate or mono- or dimethyl polyphosphates since the process of the invention proceeds equally well when trimethyl phosphate is used in the absence of methanol.

The process of the invention may be carried out by first admixing the phosphorus pentoxide or polyphosphoric acid with the methanol or trimethyl phosphate using conventional techniques and apparatus. The admixture of methanol with phosphorus pentoxide or polyphosphoric acid results in an exothermic reaction. Preferably admixture of methanol with the phosphorus pentoxide is over a period of time so as to maintain the reaction mixture at a temperature of less than circa 60° C. to 70° C. Alternatively, the reaction mixture may be cooled using conventional cooling means while admixture of methanol proceeds.

Alternatively, the phosphorus pentoxide of polyphosphoric acid is heated to a temperature less than the maximum desired process temperature, and the methanol or trimethyl phosphate added by conventional means.

The proportions of phosphorus pentoxide and methanol or trimethyl phosphate admixed are within the ratio of from about 1:1 to about 1:2.2. If higher proportions of methanol or trimethyl phosphate are employed, the product obtained is dimethyl ether rather than the desired hydrocarbons. There is no advantage in employing higher proportions of phosphorus pentoxide.

The process of the invention is carried out by heating the mixture of phosphorus pentoxide and methanol or trimethyl phosphate at a temperature of from about 185° C. to about 300° C., preferably from about 190° C. to about 220° C. and most preferably at about 200° C. At the lower temperature, reaction is slow while at the higher temperature carbonization increases and yield decreases. At 200° C., the most advantageous reaction times, yields and avoidance of carbonization occur.

The process of the invention proceeds satisfactorily at atmospheric pressures. Super-atmospheric pressures may be employed, but any advantage is mediated by the increased hazards and expense of high-pressure apparatus.

The conversion of the methanol or trimethyl phosphate to hydrocarbons is generally complete in from about 1 to about 8 hours, depending on the temperature employed in the process. The process is completed more rapidly at the higher temperatures. At the preferred temperature range, the reaction is substantially complete in from about 4 to about 8 hours. Completion of the conversion may be observed visually since the hydrocarbon mixture product separates from the reaction mixture as a colorless liquid. Completion of the reaction is indicated when no more product separates. The product may be separated as formed by distillation technique or allowed to accumulate as a gently refluxing supernatent layer. Upon completion of the reaction, the supernatent hydrocarbon mixture may then be separated by decantation.

If desired, the constituency of the product hydrocarbon mixture obtained as a supernatent layer in the reaction mixture can be altered by continued refluxing of the reaction mixture after the conversion of methanol or trimethyl phosphate is complete. By continued refluxing of the hydrocarbon product with the reaction mixture, lower molecular weight hydrocarbons in the product mixture are converted to higher molecular weight hydrocarbons. This is desirable when a heavy hydrocarbon oil is desired.

The following examples describe the manner and process of making and using the invention and set forth the best mode contemplated by the inventor of carrying out the invention but are not to be construed as limiting.

EXAMPLE 1

An appropriate vessel is charged with 100 gms. of polyphosphoric acid (circa 84 percent by weight phosphorus pentoxide). To the charge there is added with stirring 72 ml. of trimethyl phosphate. The resulting mixture is heated to a temperature of 190° C. and refluxed at that temperature for about 4 hours with continued stirring. At the end of this period, the reaction mixture is in two phases, the upper, supernatent layer being a colorless oily layer which gently refluxes. The mixture is cooled in a solid carbon dioxide bath and the clear upper layer decanted to obtain 9 gms (36 percent yield based on starting trimethyl phosphate) of a mixture of hydrocarbons. About 200 different compounds are found in the mixture. Gas-liquid chromatography indicates a hydrocarbon distribution as follows: $C_4$ compounds, 4.2 percent; $C_5$ compounds, 11.8 percent; $C_6$ compounds, 21.5 percent; $C_7$ compounds, 27.3 percent; $C_8$ compounds, 15.5 percent; $C_{9+}$ compounds, 19.7 percent. The largest fraction, i.e.; $C_7$ compounds contain 2-methylhexane (6.9 percent); 2,3-dimethylpentane (5.1 percent); 3-methylhexane (6.8 percent); heptane (0.4 percent) and substituted cyclopentanes. The $C_{9+}$ fraction contains compounds of empirical formulae $C_n H_{2n-4}$ up to $C_n H_{2n-10}$. The monoaromatic compounds $C_n H_{2n-6}$ are all highly substituted and maximal at $C_{12}$. Almost all fractions contain small amounts of alkenes, e.g. circa 0.6 percent of methylcyclohexene in the $C_7$ fraction.

The hydrocarbon mixture so obtained is combustible and may be employed, for example, as a heating fuel by combustion in an appropriate heating apparatus.

EXAMPLE 2

The transverse portion of a ⅜" "U" tube (7 inches between vertical portions) is filled with phosphorus pentoxide and immersed in a pan of Wood's metal heated to a temperature of 300° C. By drop-wise addition, 60 ml. of methanol is charged to one vertical end of the tube and carried through the bed of phosphorus pentoxide by a stream of nitrogen gas. The opposite vertical portion of the tube discharges into a collection vessel cooled in dry ice. After 65 minutes, addition of methanol is complete and there is collected in the collection vessel 25 ml. of a liquid mixture of hydrocarbons. Gas-liquid chromatography carried out on an aliquot of the product obtained gives a spectra as shown in FIG. 1.

EXAMPLE 3

The transverse portion of a ⅜ inch "U" tube (7 inches between vertical portions) is filled with phosphorus pentoxide and immersed in a pan of Wood's metal heated to a temperature of 260° C. By drop-wise addition, 100 ml. of methanol is charged to one vertical end of the tube and carried through the bed of phosphorus pentoxide by a stream of nitrogen gas. The opposite vertical end discharges into a collection vessel cooled in dry ice. After about one hour addition of methanol is complete and about 30 ml. of a liquid mixture of hydrocarbons is collected in the collection vessel.

EXAMPLE 4

To an appropriate vessel there is charged 350 ml. of phosphoric acid (85%). The charge is heated until 160 ml. of water distills off. The residue is a heavy liquid which is polyphosphoric acid (circa 78% by weight phosphorus pentoxide). The residue is heated to a temperature of about 260° C. and to the hot residue there is added drop-wise a mixture of 60 gms of methanol dissolved in commercially available polyphosphoric acid. During the drop-wise addition, the reaction mixture darkens and foams. A liquid hydrocarbon mixture is isolated by steam distillation.

What is claimed is:

1. A process for preparing a mixture of hydrocarbons, which comprises; heating a mixture comprising in a molar ratio of from about 1:1 to 1:2.2, phosphorus pentoxide and trimethyl phosphate to a temperature within the range of from about 185° C. to about 300° C.

2. A process according to claim 1 wherein said phosphorus pentoxide is provided in polyphosphoric acid.

3. A process according to claim 2 wherein said polyphosphoric acid contains from about 78% to about 84% by weight of said phosphorus pentoxide.

4. A process according to claim 1 which additionally comprises refluxing the mixture of hydrocarbons obtained after the conversion of the compound selected to obtain a mixture of higher molecular weight hydrocarbons.

5. A process for preparing a mixture of hydrocarbons, which comprises; heating a mixture comprising in a molar ratio of from about 1:1 to 1:2.2, phosphorus pentoxide and a compound selected from the group consisting of methanol, trimethyl phosphate and mixtures thereof, to a temperature within the range of from about 190° C. to 220° C.

6. A process according to claim 5 wherein said phosphorus pentoxide is provided in polyphosphoric acid.

7. A process according to claim 5 wherein said compound is methanol.

8. A process according to claim 5 wherein said compound is trimethyl phosphate.

9. A process for preparing a mixture of hydrocarbons, which comprises; heating a mixture comprising in a molar ratio of from about 1:1 to 1:2.2, phosphorus pentoxide and a compound selected from the group consisting of methanol, trimethyl phosphate and mixtures thereof, to a temperature within the range of from about 185° C. to about 300° C., said heating being carried out under atmospheric pressure.

10. A process according to claim 9 wherein said phosphorus pentoxide is provided in polyphosphoric acid.

11. A process according to claim 9 wherein said compound is methanol.

12. A process according to claim 9 wherein said compound is trimethyl phosphate.

* * * * *